US006187540B1

(12) United States Patent
Staub et al.

(10) Patent No.: US 6,187,540 B1
(45) Date of Patent: Feb. 13, 2001

(54) METHOD OF NEWBORN IDENTIFICATION AND TRACKING

(75) Inventors: Rick Staub, Sugar Land; Caroline Caskey, Houston, both of TX (US)

(73) Assignee: Identigene, Inc., Houston, TX (US)

( * ) Notice: Under 35 U.S.C. 154(b), the term of this patent shall be extended for 0 days.

(21) Appl. No.: 09/189,156

(22) Filed: Nov. 9, 1998

(51) Int. Cl.[7] .............................. C12Q 1/68; C12P 19/34
(52) U.S. Cl. ......................... 435/6; 435/91.2; 435/287.2; 435/287.3; 435/307.1; 206/1.5; 220/200; 220/315
(58) Field of Search ............................ 435/6, 91.2, 810, 435/287.2, 287.3, 307.1; 220/315, 200; 206/1.5, 807

(56) References Cited

U.S. PATENT DOCUMENTS

| | | | |
|---|---|---|---|
| 5,413,908 | * 5/1995 | Jeffreys | 435/6 |
| 5,445,934 | 8/1995 | Fodor | 435/6 |
| 5,484,060 | 1/1996 | Middle | 206/438 |
| 5,529,202 | 6/1996 | Shamis | 220/301 |
| 5,561,071 | 10/1996 | Hollenberg | 437/1 |
| 5,571,639 | 11/1996 | Hubbell | 430/5 |
| 5,593,839 | 1/1997 | Hubbell | 435/6 |
| 5,599,668 | 2/1997 | Stimpson | 435/6 |
| 5,605,662 | 2/1997 | Heller | 422/68.1 |
| 5,608,382 | 3/1997 | Webb | 340/573 |
| 5,632,957 | 5/1997 | Heller | 422/68.1 |
| 5,671,303 | 9/1997 | Shieh | 385/12 |
| 5,728,532 | 3/1998 | Ackley | 435/6 |
| 5,731,152 | 3/1998 | Maracas | 435/6 |
| 5,733,509 | 3/1998 | Ackley | 422/131 |
| 5,733,729 | 3/1998 | Lipshutz | 435/6 |
| 5,741,644 | 4/1998 | Kambara | 435/6 |
| 5,756,126 | 5/1998 | Burgoyne | 424/488 |
| 5,763,599 | 6/1998 | Pfleiderer | 536/55.3 |
| 5,785,044 | * 7/1998 | Meador et al. | 128/760 |
| 5,795,716 | 8/1998 | Chee | 435/6 |
| 5,821,060 | 10/1998 | Arlinghaus | 435/6 |
| 5,827,482 | 10/1998 | Shieh | 422/82.02 |

FOREIGN PATENT DOCUMENTS

| | | |
|---|---|---|
| 2273266A | 6/1994 | (GB) . |
| WO 98/18111 | 4/1998 | (WO) . |

OTHER PUBLICATIONS

Lopez–Valverde et al. Prog. Obstel Ginecol. 1998. 41:443–449, Oct. 1998.*
Hochmeister et al. Archiv Fur Kriminologie. 200:8113–120, Oct. 1998.*
Abstract: Caggana M., et al., Rapid Efficient Method for Multiplex Amplification from Filter Paper, Hum. Mutat. (1998) 11(5): 404–9.
Abstract: Descartes M., et al., Genotypic Confirmation from the Original Dried Blood Specimens in a Neonatal Hemoglobinopathy Screening Program, Pediatr. Res. (1992) 31(3): 217–21.

Abstract: Fauser S. & Wissinger B., Simultaneous Detection of Muliple Point Mutations using Fluorescence–coupled Competitive Primer Extension, Biotechniques (1997) 22(5): 964–8.
Abstract: Fox S.A., et al., Rapid Genotyping of Hepatitis C Virus Isolates by dideoxy Fingerprinting, J. Virol. Methods(1995) 53(1): 1–9.
Abstract: Griffin H. G. & Griffin A. M., DNA Sequencing. Recent Innovations and Future Trends, Appl. Biochem. Biotechnol. (1993) 38(1–2): 147–59.
Abstract: Hacia J.G., et al., Evolutionary Sequence Comparisons using High–density Oligonucleotide arrays. Nat. Genet. (1998) 18(2): 155–8.
Abstract: Hacia J. G., et al., Detection of Heterozygous Mutations in BRCA1 using High Density Oligonucleotide Arrays and Two–colour Fluorescenc Analysis, Nat. Genet. (1996) 14(4): 441–7.
Abstract: Haff L. A. Smirnov I. P., Single–nucleotide Polymorphism Identification Assays using a Thermostable DNA Polymerase and Delayed Extraction MALDI–TOF mass spectrometry, Genome Res. (1997) 7(4): 378–88.
Abstract: Hochmeister M., et al., A Foldable Cardboard Box for Drying and Storage of by Cotton Swab Collected Biological Samples, Arch. Kriminol. (1997) 200(3–4): 113–20.
Abstract: Hochmeister M., et al., Applications of Forensic DNA Technolgoy in Gynecologic Practice, Gynakol. Geburtshilfliche Runsch. (1994) 34(4): 206–19.
Abstract: Kirpekar F., et al., DNA Sequence Analysis by Maldi Mass Spectrometry, Nucleic Acids Res. (1998) 26(11): 2554–9.
Abstract: Lan L. et al., The Analysis of Human DNA Fingerprints by the Synthetic Oligonucleotide Probe, I Chuan Hsueh Pao (1993) 20(1):1–6.
Abstract: Livache T. et al., Polyrrole DNA chip on a Silicon Device: Example of Hepatitis C Virus Genotyping Anal., Biochem. (1998) 255 (2): 188–94.
Abstract: McCabe E.R., et al., DNA Microextraction from Dried Blood Sports on Filter Paper Blotters: Potential Applications to Newborn Screening, Hum. Genet. (1987) 75(3): 213–6.
Abstract: Pastinent T., et al., Minisequencing: a Specific Tool for DNA Analysis and Diagnostics on Oligonucleotide Arrays, Genome Res. (1997) 7(6): 606–14.
Abstract Pease A.C. et al., Light generated Oligonucleotide Arrays for Rapid DNA Sequence Analysis, Proc. Natl. Acad. Sci. USA (1994) 91(11): 5022–6.
Rodrigues J., et al. la Huella And en Lugar de la Huella Plantar en la Identificacion Neonatal, Medicina Clinica (1996) 107(4): 121–3.

(List continued on next page.)

Primary Examiner—Carla J. Myers
(74) Attorney, Agent, or Firm—Jenkens & Gilchrist

(57) ABSTRACT

A method of ensuring that each newborn infant is identified at birth and maintaining the correct newborn and mother pairing at least until discharge of the mother and child. The method involves genotyping the infant and/or birth mother at one or more times.

20 Claims, No Drawings

OTHER PUBLICATIONS

Abstract: Rubin E.M., et al., Alaron Newborn Screening by DNA Analysis of Dried Blood Spots. Hum. Genet. (1989) 82(2): 134–6.

Abstract: Schena M., et al., Parallel Human Genome Analysis: Microarray–based Expression Monitoring of 1000 genes, Proc. Natl. Acad. Sci. USA (1996) 93(20): 10614–9.

Abstract: Southern E.M., DNA Chips: Analysing Sequence by Hybridization to Oligonucleotides on a Large Scale, Trends Genet. (1996) 12(3): 110–5.

Abstract: Stimpson D. I., et al., Real–time Detection of DNA Hybridization and Melting on Oligonucleotide arrays by using Optical Wave Guides, Proc. Natl. Acad. Sci. USA (1995) 92(14): 6379–83.

Abstract: Tang K., et al., Matrix–assisted Laser Desorption/ionization Mass Spectrometry of Immobilized Duplex DNA probes, Nucleic Acids Res. (1995) 23(16): 3126–31.

Abstract: Taranenko N. I., et al., Laser Desorption Mass Spectrometry for Point Mutation Detection, Genet. Anal. (1996) 13(4): 87–94.

Abstract: Wang J. et al., Nucleic–acid Immobilization, Recognition and Detection at Chronopotentiometric DNA chips, Biosens. Bioeletron, (1997) 12(7): 587–99.

Abstract: Wang D. G., et al., Large–scale Identification, Mapping and Genotyping of Single–nucleotide Polymorphism in the Human Genome, Science (1998) 280 (5366): 1077–82.

Abstract Xu L., et al. Electrophore Mass tag Dideoxy DNA sequencing, Anal. Chem. (1997) 69(17): 3595–602.

Abstract: Zhang Y. H. & McCabe E. R., RNA Analysis from Newborn Screening Dried Blood Specimens Hum. Genet. (1992) 89(3): 311–4.

Butz A.M., et al., Newborn Idenification: Compliance with AAP Guidelines for Perinatal Care, Clinical Pediatrics (1993) 111.

de Pancorbo M.M. et al., Newborn Genetic Identification: A Protocol Using Microsatellite DNA as an Alternative to Footprinting, Clin. Chim. Acta (1997) 263(1): 33–42.

Heckman, M. et al., Quality Improvement Principles in Practice: The Reduction of Umbilical Cord Blood Errors in the Labor and Delivery Suite: Interdisciplinary Performance Improvement, J. Nursing Care Quality (1998) 3(12): 47.

Shumaker et al., Mutation Detection by Solid Phase Primer Extension, Hum. Mutation (1996) 7:346–54.

* cited by examiner

METHOD OF NEWBORN IDENTIFICATION AND TRACKING

SUMMARY OF THE INVENTION

The present invention relates to a method of uniquely identifying a newborn and mother pair at the birth of a child in a hospital-like setting and ensuring that the newborn/mother pairing has been correctly maintained at least until discharge of the mother and child pair. The invention also provides a unique sample collection means that prevents samples from being mislabeled or incorrectly associated with a non-family member and can be permanently stored for future identification purposes.

DESCRIPTION OF THE BACKGROUND

Identification of infants at birth is a critical issue for hospitals, birthing centers and other institutions where multiple births occur. With approximately 300,000 infants born worldwide each day, a large hospital may experience over one hundred new births each day. A large hospital may see as many as a hundred new infants each day. Correct identification of infants is essential to ensure that each mother travels home with her own child.

In the past infants have been identified by means of footprints. However, this is not a satisfactory method of identifying infants because there is no means of ensuring that a footprint is associated with a particular mother, other than placing a footprint in the mother's hospital records. Further, footprints of newborn infants are difficult to take and difficult to distinguish. Additionally, the footprints are useful for only a short period in identifying the infant and will not suffice as a permanent identification means.

Current identification technologies generally consist of attaching an identification device to the newborn with a matching device for the mother. Before an infant can be moved from the hospital, the devices are compared to ensure that only the mother of that infant can leave with the child. Such devices include the typical wrist bands or bracelets, which today are often electronically readable (see e.g., WO98/18111). In another variation, the mother wears a wrist band, but the infant has an umbilical clamp (see e.g., U.S. Pat. No. 5,484,060 and U.S. Pat. No. 5,608,382) and in yet another variation, the infant is actually marked with a semi-permanent ink (see e.g., GB2,273,266 and U.S. Pat. No. 5,484,060).

However, any device or external labeling means can be intentionally defeated, by changing the markings or electronic signature on the existing device, or by completely replacing the device with an appropriately marked device. Recently, it was discovered in the United States that two infants were switched at birth. Evidence strongly suggested that the switching was not accidental. Tragically, the switch was not discovered for several years and might not ever have been discovered absent a paternity contest involving one of the children. In its aftermath, the event leaves considerable consternation about how to cope with child custody issues, visitation rights, hospital liability, and an ongoing criminal investigation.

Public concern over this issue is significant. A recent market survey created by an academic institution was conducted on 200 expectant mothers to assess their interest in a service that would assure them that their infants had not been switched at birth. An overwhelming 85% of the respondents wanted such a service and would be willing to pay for it. Public concern has also reached the U.S. Congress. Proposed legislation entitled "The Infant Protection and Baby Switching Prevention Act of 1998" (H.R. 4680) has been introduced into the House of Representatives in an effort to require hospitals to address this problem. Unfortunately, no specific solution was recommended in the Act.

Therefore, although rare, infant switches do occur and with potentially devastating consequences. A failsafe method of uniquely identifying which infant belongs to which mother is urgently required. Such system should be tamper-proof, simple, easy, and cost effective. Furthermore, the ideal system would create a permanent record allowing for future identification of the child in the event of abduction or accident.

Genotyping has been used to identify paternity, and occasionally maternity, where contested, usually in a child support context. Genotyping has also been suggested and used after the fact where it is suspected that infants have been switched. See e.g., de Pancorbo M. M., et al., Newborn Identification: A Protocol Using Microsatellite DNA as an alternative to Footprinting, CLIN. CHIM. ACTA (1997) 263(1): 3342. However, to date no one has applied genotyping technology to systematically identify infants at birth and again at discharge to ensure that no switching has occurred and that the infant has been correctly paired with its birth mother. Furthermore, no one has provided a permanent storage mechanism for future identification purposes.

Such massive genotyping efforts have never been applied in a hospital setting and present significant logistical concerns. It would not suffice, for example, for a sample to be merely collected and later typed within the hospital environment because such a process is subject to the same labeling errors that currently exist with neonatal samples such as cord blood samples. See e.g., Heckman, Maria, et al., Quality Improvement Principles in Practice: The Reduction of Umbilical Cord-Blood Errors in the Labor and Delivery Suite; Interdisciplinary Performance Improvement, J. NURSING CARE QUALITY (1998) 3(12): 47 (noting that in the eight months prior to their process improvement efforts there were 18 mislabeled specimens out of 3,504 births—an error rate of 0.5%).

SUMMARY OF THE INVENTION

The only failsafe method of identifying correct infant/mother pairing is by genetic typing of the infant and/or the putative mother. However, prior to the present invention, no one has routinely employed genotyping for this purpose or devised a simple, inexpensive system that can be routinely performed at birth and/or at discharge. The method of the present invention has the benefit that even if the hospital records are incorrect or have been intentionally altered, such an event will be indicated and an infant/mother pairing can still be correctly determined.

In one embodiment, the invention is a method for ensuring that a newborn/mother pairing is correct at discharge. The method comprises obtaining a first sample of newborn cells at the birth of a newborn. The sample is stored on a tamper-proof collection device, forwarding to a genotyping location, and examined to ensure that tampering has not occurred. The first sample is genotyped to provide a first newborn fingerprint. Likewise, a second sample of newborn cells is obtained and treated as the first sample. The first and second newborn fingerprints are compared, and substantial identity of the two fingerprints indicates that said newborn has not been switched prior to discharge.

The tamper-proof collection device may also be stored in a dry, dark location for possible future use. Sample of newborn cells may be obtained from a buccal swab, blood, cord blood, amniotic fluid, embryonic tissue, hair, or fingernail clipping. Cells may be collected at birth or prior thereto.

In an additional embodiment, at least one sample of maternal cells from a mother is collected as above. It is genotyped to provide a maternal fingerprint, and comparison of the maternal fingerprint and said first or second newborn fingerprints indicates maternity where there is evidence for transmittance of an allele from the mother to the infant at all marker loci studied (defined herein as "about 50% identity"). This result confirms that the newborn/mother pairing is correct.

In all cases, a report summarizing the results of the genotyping comparison can be generated and forwarded to the parents or hospital.

In another embodiment, the method comprises obtaining discharge-samples of newborn cells from a newborn and maternal cells from a mother prior to discharge, genotyping said discharge-samples to provide a discharge newborn fingerprint and a discharge maternal fingerprint and comparing the discharge newborn and maternal fingerprints. As above, where there is about 50% identity the newborn and mother are related, thus confirming that the newborn/mother pairing is correct.

The method can be modified by also obtaining a birth-sample of newborn and maternal cells at the birth of said newborn; genotyping said birth-samples to provide a birth newborn fingerprint and a birth maternal fingerprint; and comparing all four fingerprints. Substantial identity between the two newborn fingerprints and substantial identity between the two maternal fingerprints confirms that the samples have not been tampered with. About 50% identity between the newborn and the maternal fingerprints confirm that the newborn and mother are related.

Samples may be handled as above and/or stored for future use. The sample of newborn cells can be obtained from a buccal swab, blood, cord blood, amniotic fluid, embryonic tissue, hair, or fingernail clipping, and the like and the sample of maternal cells can be obtained from blood, buccal swab, hair, skin or fingernail clippings, etc. In a preferred embodiment, buccal cells are used. Furthermore, the samples may be separate samples, mixed samples, or separate samples and a mixed sample. Reports can be generated as above.

The invention also pertains to an improved sample collection device, the improvement comprising a location and label for a maternal cell sample, a location and label for a newborn cell sample and optionally, a location and label for a mixed newborn/mother cell sample or a paternal sample.

DETAILED DESCRIPTION OF THE INVENTION

About 50% identity—Because a child inherits about half its DNA from its mother, an infant and mother should have about half identity in genotype, allowing however, for rare non-mendelian events and an acceptable rate of error in data collection (for example, where gel migration varies slightly due to temperature and other factors). Thus, about 50% identity in genotype between the infant and a putative mother indicates that the infant has inherited one allele (of two) at each marker from the putative mother and the mother and infant are related.

Birth-sample—As used herein, the term "birth-sample" refers to a sample that is collected at birth, during, or prior thereto.

Birth fingerprint—As used herein the term "birth newborn fingerprint" or "birth maternal fingerprint" refers to a DNA genotype that is ascertained from a birth-sample. Likewise a "discharge fingerprint" refers to genotypes determined from a discharge-sample.

Collection device—Any device that can be used to collect and store samples, including Guthrie cards, tubes, swabs, papers, slides, containers and the like. Such devices can be made tamper-proof with the inclusion of seals and the like. In a preferred embodiment, collection devices are modified to allow for the collection and labeling of multiple samples.

Discharge-sample—As used herein the phrase refers to a sample that is collected shortly before or during the discharge process.

Genetic typing—Also genotyping, fingerprinting, DNA typing, or any similar phrase. The term includes the use of any means known to those skilled in the art for determining an individual's genotype. For example, techniques can be nucleic acid based including size fractionation, allele specific oligonucleotide (ASO) hybridization, sequencing, restriction fragment length polymorphism (RFLP) analysis, denaturation temperature analysis, mass spectrometry analysis, etc. The methodologies are numerous, continually developing, and cannot be detailed herein. The reader is referred to the references cited herein for details.

Marker—Also polymorphism. Any sequence in the genome that is known to vary between individuals. For example, the IL-IRN gene has a marker that consists of a variable number of tandem repeats (VNTR). To date, this marker is thought to have five alleles. A single base polymorphism is also called an "SNP"—single nucleotide polymorphism. There are a variety of marker types, including VNTRs, simple tandem repeats (STRs), complex tandem repeats (CTRs), SNPs, microsatellites, etc.

Newborn/mother pair—Also infant/mother pair or any similar phrase. Refers to a mother and her own newborn infant.

Newborn/mother pairing—Refers to the assignment of a mother and infant to each other.

Newborn fingerprint—A unique genetic fingerprint or genotype corresponding to a newborn.

PCR—Polymerase chain reaction. A method of amplifying small amounts of DNA for ease of analysis. Many variations of the basic amplification protocol are well known to those of skill in the art.

Substantial identity—As used herein, the term means that samples show the same genotypes, but nonetheless accommodates an acceptable rate of error in data collection.

Generally speaking, the invention is directed to methods and devices associated with same for the failsafe identification of infants to ensure that the correct infant is sent home with a given mother. The invention involves genotyping the infant, and/or the mother, one or more times to ascertain that no switching has occurred.

In its simplest embodiment, only the newborn's cells are sampled at birth. The sample is collected onto a tamper-proof card and placed into a lock box for routine transfer to an independent laboratory for subsequent testing. The sample is labeled with both mother and newborn names and preferably is initialed by a hospital witness to ensure that the sample on the card was collected from the newborn at birth. A similar sample is collected at discharge and both samples are sent to an independent laboratory for analysis. In this system, it is important that the sample cards are rendered tamper-proof to ensure that samples have not been compromised.

In the independent test laboratory, all samples from a given institution are typed and for each pair of birth/discharge samples, a report is produced that can be provided to the parents which assures them that the infant birthed is the same child the parent brought home. If there is some discrepancy in the two samples, it may be possible to compare against all of the samples from a given institution and/or obtain additional maternal samples to ensure correct pairing. Thus, this system provides an important, yet cost effective back-up means of accurately identifying infants.

This embodiment is particularly preferred where simple and fast genotyping technologies have not yet been established in a given hospital. In this way, the hospital gains the assurance that only a genotype can provide without having to implement a new series of process steps. However, this embodiment, although the simplest, is still subject to errors created by intentional mislabeling of samples. Thus, this embodiment is best suited as a backup system for the existing bracelet or cord clamp systems and not a replacement system. As indicated above, some 85% of expectant parents indicated they would be willing to pay for such a service and this simple embodiment is both cost effective and minimally intrusive. However, even in this embodiment, it may be preferred that both maternal and newborn cells are sampled in order to ensure that effects of intentional labeling errors are minimized, as described herein.

In a second embodiment, newborn and maternal samples are collected prior to discharge, and as above, may be sent off-site for analysis. Both samples are collected onto a single card, thus minimizing the effects of mislabeling errors. This methodology ensures that the correct newborn/mother pairing occurred at discharge. As above, a report can be generated and sent to the anxious parent.

These embodiments are simple embodiments and are cost effective with current technology. However, because there is the possibility of intentional mislabeling of samples, they are not appropriate as a system to replace existing infant identification means, but function rather as a safeguard to ensure that the existing methodology has not been tampered with. In order to use genotyping as a method in replacement of the existing bracelet/cord clamp identification technologies, it is felt that additional redundancies are required.

Therefore, a more sophisticated embodiment, cells of both the mother and the child are sampled and typed to create a unique newborn/mother genetic fingerprint. This unique newborn/mother fingerprint can be electronically coded into the existing bracelet or cord clamp devices and/or merely stored under normal record keeping procedures. Prior to discharge of the pair, additional cell samples can be collected and retyped to ensure that the correct pairing has been maintained and that the child has not been switched with another. Variations between the initial and subsequent newborn/mother fingerprints indicate that switching, an error in data analysis, or an error in recordation may have occurred and suggest additional data analysis. If necessary, a more detailed genome analysis of the putative mother and child will conclusively establish correct pairing.

This particular embodiment of the invention is technically feasible with current technology, but is not yet cost effective for routine screening. However, with the rapid development of existing genetic analysis technologies, it will soon be feasible to have an automated machine on site in every hospital which can rapidly take and confirm genotypes.

In another embodiment, the method comprises of three types of DNA samples; a maternal sample; a newborn sample and a mixed sample. The mixed sample acts as an internal control to ensure that the maternal and newborn samples have been correctly assigned to each other upon typing. However, a single mixed sample or only the separate maternal and newborn samples may also be employed. Mixed DNA samples are readily obtainable form a variety of sources, including blood, cord blood, amniotic fluid or any other tissue which has a mixture of both fetal and maternal cells or genetic material. Alternatively, separate samples of each may be manually mixed. Of course, it is also possible to add paternal samples to the collection cards as well. However, because of the potential sensitivity of paternity, this may not be appropriate for routine use, but can be provided on request.

The taking of samples at birth need not await complete delivery of the newborn. In fact, the genotyping analysis can begin prior to birth by sampling the amniotic fluid, or other maternal/embryonic tissues. This may even be preferred as the genotyping process itself can reasonably be expected to require at least an hour, even with the most sophisticated of current technologies. Thus, the taking of samples "at birth" expressly contemplates and includes fetal sampling. One particularly useful means of establishing a mother/child fingerprint is with the use of fetal cell sorting to separate the fetal cells that are found in the maternal bloodstream. With this technology, the pair can be safely typed before delivery without risk to the fetus. This procedure helps to eliminate the necessity of additional tests during delivery, at a time when the minimization of extraneous activities is desirable.

All samples may be stored for future use. One easy reliable means of storing blood, for example, is on the Guthrie card generally used for newborn screening of inborn errors of metabolism. Whole blood is collected on filter paper, dried and stored at room temperature. The use of a single card, specially designed for collecting infant and mother blood samples will ensure that the samples are always associated and cannot be separated. Alternatively, blood samples may be mixed and contained in a single collection device or tube.

A Guthrie-like card that contains separate sample collection spaces and labeling indicia so that maternal and newborn samples may be collected on the same card has been designed. If desired, a space can be included for paternal samples as well. The use of a single card for the collection of samples ensures that samples cannot be inadvertently associated with a non-family member and helps to eliminate at least one source of error.

The multiple-use card especially helps to eliminate errors in those institutions where an infant record is not created until after the birth of the infant. Thus, upon sample collection there is a period of awaiting a hospital record number before a given sample can be correctly labeled and this is an important source of mislabeling errors in the process. In those hospitals where an infant record is created at the time of admitting the expectant mother, this is not an issue and the sample can be correctly labeled at the onset.

It is strongly suggested that preprinted maternal and newborn labels, coded to show the relationship, be created on admittance of the expectant mother and used throughout the hospital stay. This additional level of automation will ensure that the sample collection card is correctly labeled. However, even in the event of labeling errors in those hospitals that lack such process measures, the presence of both samples on a single card is an improvement over separate samples because in the event of complete labeling or record failure, the samples on the cards can still be typed and infants matched to mothers on the basis of genotype. Further, the inclusion of a mixed sample provides an important internal positive control.

Another preferred sample type is that obtained by a buccal swab. This may be preferred for pre-discharge sample collection because it is painless to collect. Additionally, protocols using these specimen types show superiority to those using blood specimens in the areas of collection, transport, storage and overall cost. Further, PCR amplifications of DNA collected by buccal swab are not subject to inhibition by heme. A dried buccal swab is amenable to subsequent DNA analysis for at least five years and it is expected that samples will be preserved for as long as they are kept dry and away from the light.

Buccal samples are collected onto cotton or sponge swabs which can then be blotted onto FTA paper. Alternatively, the samples are stored on cardboard folders (see e.g., Hochmeister M, et al., A foldable cardboard box for drying and storage of by cotton swab collected biological samples, ARCH. KRIMINOL. (1997) 200(3–4):113–20) or on flat slide-like sheets which may or may not be provided with some type of protective covering. A hinged or bifold sheet has been designed which may be substantially flat on its top and bottom surfaces or may have depressions in the bottom surface into which the sample can be placed. The sheet can be made of paper or membrane if flat and may also be made of plastic where depressions are preferred, or may be any other material that does not interfere with subsequent sample extraction. The trifold paper collection card with a tab on one side that allows for vertical storage e.g., with the tab protruding up from the stacked cards to allow ease of identification, is preferred as both inexpensive and space conserving. Other sample collection and storage means are described in U.S. Pat. No. 5,756,126, Like the Guthrie card, these collection devices are modified to allow for multiple sample collection and labeling.

The genetic typing may be performed on genomic DNA, mitochondrial DNA or may be based on typing the RNA present in a cell. See e.g., Zang Y. H. & McCabe E. R., RNA Analysis from Newborn Screening Dried Blood Specimens, HUM. GENET. (1992) 89(3): 311–4. Further, the typing methodology may be any that is currently used in the art, including techniques that are sequence based, size analysis based, hybridization based or a combination thereof. Generally, DNA samples may be amplified before analysis in a PCR or PCR-like reaction. Genetic typing methodologies are well known and need not be detailed herein.

A particularly powerful means of analyzing genetic information is DNA chip technology. Generally speaking, DNA chips comprise an array of oligonucleotide probes. Conditions can be established such that nucleic acid will only hybridize to a given probe if a perfect match is found. The array can comprise thousands of oligonucleotides and the use of automated scoring techniques and sophisticated data analysis software allow the collection of large amounts of data very quickly. (see e.g., U.S. Pat. No. 5,827,482; U.S. Pat. No. 5,821,060; U.S. Pat. No. 5,795,716; U.S. Pat. No. 5,763,599; U.S. Pat. No. 5,741,644; U.S. Pat. No. 5,733,729; U.S. Pat. No. 5,733,509; U.S. Pat. No. 5,731,152; U.S. Pat. No. 5,728,532; U.S. Pat. No. 5,671,303; U.S. Pat. No. 5,632,957; U.S. Pat. No. 5,605,662; U.S. Pat. No. 5,599,668; U.S. Pat. No. 5,593,839; U.S. Pat. No. 5,571,639; U.S. Pat. No. 5,561,071; and U.S. Pat. No. 5,445,934; See also; Wang D. G., et al., Large-scale identification, mapping, and genotyping of single-nucleotide polymorphisms in the human genome, SCIENCE (1998) 280 (5366): 1077–82; Hacia J. G., et al., Evolutionary sequence comparisons using high-density oligonucleotide arrays, NAT. GENET. (1998)18(2): 155–8; Livache T., et al., Polypyrrole DNA chip on a silicon device: example of hepatitis C virus genotyping, ANAL. BIOCHEM. (1998) 255 (2): 188–94; Pastinen T., et al., Minisequencing: a specific tool for DNA analysis and diagnostics on oligonucleotide arrays, GENOME RES. (1997) 7(6): 606–14; Wang J., et al., Nucleic-acid immobilization, recognition and detection at chronopotentiometric DNA chips, BIOSENS. BIOELECTRON. (1997) 12 (7): 587–99; Hacia J. G., et al., Detection of heterozygous mutations in BRCA1 using high density oligonucleotide arrays and two-colour fluorescence analysis, NAT. GENET. (1996) 14(4): 441–7; Schena M., et al., Parallel human genome analysis: microarray-based expression monitoring of 1000 genes, PROC. NATL. ACAD. SCI. USA (1996) 93(20): 10614–9; Southern E. M., DNA chips: analysing sequence by hybridization to oligonucleotides on a large scale, TRENDS GENET. (1996) 12(3): 110–5; Stimpson D. I., et al., Real-time detection of DNA hybridization and melting on oligonucleotide arrays by using optical wave guides, PROC. NATL. ACAD. SCI. USA (1995) 92(14): 6379–83; Pease A. C., et al., Light-generated oligonucleotide arrays for rapid DNA sequence analysis, PROC. NATL. ACAD. SCI. USA (1994) 91(11): 5022–6); Shumaker et al., Mutation Detection by Solid Phase Primer Extension, HUM. MUTATION (1996) 7:346–54.

Another powerful means analyzing genetic information involves the use of mass spectrometers to identify small mass differences in PCR products that have single nucleotide polymorphisms (SNPs). Kirpekar F., et al., DNA sequence analysis by MALDI mass spectrometry, NUCLEIC ACIDS RES. (1998) 26(11): 2554–9. Gene Trace Systems, Inc., for example, is able to analyze 10,000 samples a day with an error rate of one in 10,000. With a large collection of SNPs in a multiplex PCR one can quickly and easily genotype an individual without the necessity for time consuming electrophoretic separation of samples.

Yet another means of analyzing genetic information is "dynamic allele specific hybridization" or "DASH" for short. This technique uses labeled oligonucleotides in a multiwell format that will fluoresce when the oligonucleotide exists in a double-stranded form, but not when it is single-stranded. Adding a single strand of the DNA to be tested allows the strands to hybridize. The temperature at which the strands again denature will allow identification of the base at the SNP. This technique has the advantage that it is technically simple, not requiring expensive detection devices, such as mass spectrometers.

Furthermore, it is expected that DNA sequencing and genotyping methodology will continue to evolve and will present additional viable means of quickly genotyping an individual. See e.g., Xu L., et al., Electrophore mass tag dideoxy DNA sequencing, ANAL. CHEM. (1997) 69(17): 3595–602, Haff L. A., Smirnov I. P., Single-nucleotide polymorphism identification assays using a thermostable DNA polymerase and delayed extraction MALDI-TOF mass spectrometry, GENOME RES. (1997) 7(4): 378–88; Taranenko N. I., et al., Laser desorption mass spectrometry for point mutation detection, GENET. ANAL. (1996) 13(4): 87–94; Tang K., et al., Matrix-assisted laser desorption/ionization mass spectrometry ofimmobilized duplex DNA probes, NUCLEIC ACIDS RES. (1995) 23(16): 3126–31; Griffin H. G. & Griffin A. M., DNA sequencing. Recent innovations and future trends, APPL. BIOCHEM. BIOTECHNOL. (1993) 38(1–2): 147–59; Fauser S. & Wissinger B., Simultaneous detection of multiple point mutations using fluorescence-coupled competitive primer extension, BIOTECHNIQUES (1997) 22(5): 964–8; Fox S. A., et al., Rapid genotyping of hepatitis C virus isolates by dideoxy fingerprinting, J. VIROL. METHODS (1995) 53(1): 1–9.

Any array of markers with a reasonably high probability of individualization is sufficient for these purposes. The markers can be VNTRs, STR, CTRs, SNPs, microsatellites, etc. The number of markers that can be used herein is virtually limitless and the reader is referred to GENBANK and the literature for identification of markers and which have been successfully used in genotyping methodologies.

This system is designed to identify one out of a hundred or at most one in one thousand infants. In consequence, the genotyping need not be to such exacting specifications as in a paternity suit or criminal context. Thus, while a 50 SNP set might be required for paternity testing in a legal context, a 24 SNP set would be sufficient for infant identification purposes. For example, a set of three multiplex amplifications as follows will suffice for these purposes:

| Set 1: | | | | | |
|---|---|---|---|---|---|
| METH | HSD3B | ARSB | PROS1 | ADH3 | BCL2 |
| LPL | LDLR | IGF2 | PRP | (D21S13) | (APOB) |
| Set 2: | | | | | |
| FUT1 | DUF-1 | D2S1301 | D3S2344 | WI-1417 | TCRVB17 |
| D7S1760 | (D2S1415) | (D10S1257) | | | |
| Set 3: | | | | | |
| CPT1 | DNASE1 | CETP-1 | COL2A1 | APOC3 | CA2 |
| TCRVB12 | (EK2) | | | | |

( ) not currently used.

All publications cited herein are expressly incorporated by reference. The specification and examples should be considered exemplary only with the true scope and spirt of the invention suggested by the following claims.

It is noted that all documents referenced herein are incorporated herein by such reference for all purposes whatsoever.

What is claimed is:

1. A method for systematically ensuring that all newborn/mother pairings are correct at discharge, said method comprising:
    a) obtaining a first sample of newborn cells at the birth of each newborn in a hospital;
    b) storing said first sample in a tamper-proof collection device;
    c) forwarding said tamper-proof collection device to a genotyping location; and
    d) examining said tamper-proof collection device to ensure that tampering has not occurred;
    e) genotyping said first sample to provide a first newborn fingerprint;
    f) obtaining a second sample of cells from said each newborn in a hospital prior to discharge and handing said second sample in accordance with steps b, c and d;
    g) genotyping said second sample to provide a second newborn fingerprint; and
    h) comparing each of said first and second newborn fingerprints, wherein substantial identity of the first and second newborn fingerprints indicates that said newborn/mother pairing is correct at discharge.

2. The method of claim 1, further comprising the step of storing said tamper-proof collection device for possible future use.

3. A method as in claim 1, wherein said sample of newborn cells is obtained from a buccal swab, blood, cord blood, amniotic fluid, embryonic tissue, hair, or skin.

4. A method as in claim 1, further comprising the steps of:
    a) obtaining at least one sample of maternal cells from a mother and handling said sample of maternal cells in accordance with steps b, c and d of claim 1;
    b) genotyping said sample of maternal cells to provide a maternal fingerprint; and
    c) comparing said maternal fingerprint and said first or second newborn fingerprints, wherein about 50% identity between the maternal fingerprint and the first or second newborn fingerprints indicates that the newborn/mother pairing is correct.

5. The method of claim 1, further comprising the step of generating a report comprising a summary of said comparison.

6. The method of claim 4, further comprising the step of generating a report comprising a summary of said comparisons.

7. A method for systematically ensuring that each newborn and mother are related at discharge, said method comprising:
    a) obtaining discharge samples of newborn cells from each newborn in a hospital and maternal cells from each mother in a hospital prior to discharge; p1 b) genotyping each of said discharge-samples to provide a discharge newborn fingerprint and a discharge maternal fingerprint; and
    c) comparing each of said discharge newborn fingerprint and said discharge maternal fingerprint, wherein about 50% identity between said fingerprints indicates that said newborn and said mother are related at discharge.

8. The method of claim 7, comprising the further step of:
    a) obtaining a birth-sample of newborn and maternal cells at the birth of said newborn;
    b) genotyping said birth-samples to provide a birth newborn fingerprint and a birth maternal fingerprint;
    c) comparing said birth newborn fingerprint, said discharge newborn fingerprint, said birth maternal fingerprint, and said discharge maternal fingerprint,
        wherein substantial identity between the birth newborn fingerprint and discharge newborn fingerprint and substantial identity between the birth maternal fingerprint and discharge maternal fingerprint confirm that the samples have not been tampered with; and
        wherein 50% identity between the birth newborn fingerprints and the birth maternal fingerprints or between the discharge newborn fingerprints and the discharge maternal fingerprints confirm that the newborn and mother are related.

9. The method of claim 7, further comprising the following steps:

a) storing said discharge-samples in a single tamper-proof collection device;

b) forwarding said tamper-proof collection device to a genotyping location;

c) examining said tamper-proof collection device prior to genotyping to ensure that tampering has not occurred.

10. The method of claim 8, further comprising the following steps:

a) storing said discharge-samples and said birth-samples in two or fewer tamper-proof collection devices;

b) forwarding said tamper-proof collection devices to a genotyping location;

c) examining said tamper-proof collection devices prior to genotyping to ensure that tampering has not occurred.

11. The method of claim 9, further comprising the step of retaining said tamper-proof collection device for future use.

12. The method of claim 10, further comprising the step of retaining said tamper-proof collection devices for future use.

13. The method of claim 7, wherein said sample of newborn cells is obtained from a buccal swab, blood, cord blood, amniotic fluid, embryonic tissue, hair, or skin and wherein said sample of maternal cells is obtained from blood, buccal swab, or hair.

14. The method of claim 8, wherein said sample of newborn cells is obtained from a buccal swab, blood, cord blood, amniotic fluid, embryonic tissue, hair, or skin and wherein said sample of material cells is obtained from blood, buccal swab, or hair.

15. The method of claim 7, wherein said sample of newborn cells and maternal cells are obtained from a buccal swab.

16. The method of claim 8, wherein said sample of newborn cells and maternal cells are obtained from a buccal swab.

17. The method of claim 7, wherein said discharge-samples of newborn cells and maternal cells may be mixed with each other before analysis or may be analyzed separately.

18. The method of claim 8, wherein said discharge-samples of newborn cells and maternal cells may be mixed with each other before analysis or may be analyzed separately.

19. The method of claim 7, further comprising the step of generating a report comprising a summary of said comparison.

20. The method of claim 8, further comprising the step of generating a report comprising a summary of said comparisons.

* * * * *

UNITED STATES PATENT AND TRADEMARK OFFICE
CERTIFICATE OF CORRECTION

PATENT NO. : 6,187,540 B1
DATED : February 13, 2001
INVENTOR(S) : Rick Staub and Caroline Caskey Page 1 of 1

It is certified that error appears in the above-identified patent and that said Letters Patent is hereby corrected as shown below:

<u>Column 2,</u>
Line 20, delete "3342" and insert -- 33-42 --.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*